United States Patent [19]

Miller

[11] Patent Number: 4,760,270
[45] Date of Patent: Jul. 26, 1988

[54] METHOD OF AND APPARATUS FOR COMPARING DATA SIGNALS IN AN ELECTROOPTICAL INSPECTION SYSTEM

[75] Inventor: John W. V. Miller, Toledo, Ohio

[73] Assignee: Owens-Illinois Television Products Inc., Toledo, Ohio

[21] Appl. No.: 58,109

[22] Filed: Jun. 4, 1987

[51] Int. Cl.$^4$ ............................................. G01N 21/88
[52] U.S. Cl. ...................................... 250/563; 358/106
[58] Field of Search ............ 250/562, 563, 572, 223 B; 358/106; 356/240

[56] References Cited

U.S. PATENT DOCUMENTS

| | | | |
|---|---|---|---|
| 3,877,821 | 4/1975 | Price et al. | 250/563 X |
| 3,942,011 | 3/1976 | O'Connor | 250/223 B |
| 4,378,494 | 3/1983 | Miller | 250/563 X |
| 4,378,495 | 3/1983 | Miller | 250/223 B |
| 4,409,012 | 10/1983 | Miller | 356/446 X |
| 4,432,013 | 2/1984 | Miller et al. | 250/563 X |
| 4,467,350 | 8/1984 | Miller | 250/223 B X |

*Primary Examiner*—David C. Nelms
*Assistant Examiner*—Steven J. McGowan

[57] ABSTRACT

A system of detecting abrupt optical deviations in an object such as defects in a TV tube faceplate employing a line scan camera operated at a fixed scan frequency to feed analog video signals to a log amplifier the output of which is high-pass filtered to detect on an illumination invariant basis defect indicating deviations in light emanating from the object. The passed logarithmic deviation signals are compared with threshold signal magnitudes predetermined for the areas of the object from which the deviation signals are induced and if equal to the threshold an event signal is issued. The absolute magnitude of the event is measured by high pass filtering the analog video signal so that only the abrupt deviation from background light intensity is passed to a memory enable by the event signal. In defect analysis the size of the defect is measured as a pixel count of those pixels having signals exceeding one half the maximum pixel signal magnitude within the defect.

11 Claims, 5 Drawing Sheets

METHOD OF AND APPARATUS FOR COMPARING DATA SIGNALS IN AN ELECTROOPTICAL INSPECTION SYSTEM

This invention relates to machine vision systems and more particularly to method of and apparatus for developing useful information from electrooptically developed signals in an inspection system.

Heretofore it has been known to inspect objects by illuminating them while in an optical system and directing the resultant image to a photoelectric sensing mechanism. Where details of the inspected object are to be evaluated, such systems have employed scanning devices. Various aspects of the signals derived can be employed to develop significant information from factors such as the deviations in light intensity of an area of the image from the light intensity from other nearby areas, the size of the area of different light intensity, and the shape of the area of the deviation.

Systems such as those shown in U.S. Pat. Nos. 3,708,680 and 3,716,136, have circuitry including means for receiving and interpreting light passed through or directed onto an item subject to inspection. Such devices incorporate either a visual display for comparison of the item or employ a means capable of producing an electrical signal proportional to the intensity of light passing through, refracted from, or reflected from the item. The output of these devices is compared against a standard to determine if the item under inspection is suitable as to size and construction and is without unacceptable defects.

U.S. Pat. No. 3,877,821 discloses an apparatus having a scanning array of photosensitive devices that receives light from discrete areas of the item under inspection and is serially interrogated to generate a train of pulses having amplitudes representing the light received from the item. Adjacent pulses are compared to generate signals having amplitudes which represent the difference in pulse amplitudes. The different signals can be utilized to indicate a defect in the object being inspected. U.S. Pat. No. 3,942,001 discloses an apparatus for detecting the presence of extraneous matter or cracks in translucent containers. A beam of light is projected through the container to generate an inspection signal which is compared with an acceptance signal. The acceptance signal amplitude is varied in accordance with the position of the spot beam with respect to the container.

Glass bottles have been inspected utilizing data signals generated from a line scan camera having an aligned array of photodiodes, an optical system including a light source for directing light to a bottle and thence to the line scan camera, and means to advance bottles individually into the optical system and rotate them while in that system. A multiplicity of scans of the bottle at different rotational positions in the optical system enable all or a portion of the bottle sidewall to be inspected. Event signals, indicative of defects or foreign objects, are generated when the magnitudes of adjacent photodiode signals differ by an amount which exceeds a threshold level. Signals are also generated to identify the location of each event signal with respect to a corresponding photodiode and to identify the scan of the object in which the event signal was generated to associate the event signal with a location on the object. U.S. Pat. Nos. 4,378,494, 4,378,495, 4,432,013, 4,437,116 and 4,467,350 disclose such systems with adjuncts such as processing means for event signals to identify and evaluate adjacent defects in the same and/or adjacent scans and compare such processed signals with predetermined values to identify defects, means to display the event signals as a two-dimensional representation of the surface of the bottle as if it had been cut and unwrapped, means to set threshold values to optimize defect detection performance, paired control units to alternately process inspection data and thereby speed the inspection process with one unit processing data while the other unit receives data, and signal comparison means for minimizing general light variations across the object.

In the disclosure of U.S. Pat. No. 4,432,013 illumination invariant signals were developed by generating a comparison signal representing the deviation between two analog video signals representing light received from particular inspection points on an object being inspected. The comparison signal is generated with a magnitude representing the ratio between the values of the two video signals by converting the analog signals to digital form and then determining the log of each of the digitized video signals. The difference between the log signals is determined. The negative difference is then exponentiated to determine the ratio. Assuming the object was illuminated uniformly and that changes in illumination level were gradual, the ratio between signals from adjacent or nearby discrete areas was employed as an indicator of a defect respresented by the abrupt change in illumination at a level set at a signal threshold.

Another system utilizing a comparison signal representing the magnitude difference between two successive video signals representing adjacent inspection areas is disclosed in U.S. Pat. No. 4,437,116 where the comparison signal is generated with a magnitude representing the ratio between two successive video signals by storing the first signal until the second signal is generated and developing the ratio in a comparator. This ratio tolerated gradual changes in light intensity without affecting the value of the comparison signal.

In the disclosure of U.S. Pat. No. 4,467,350 data was devloped for electrooptical inspection by a line scan camera system by comparison of pixel ratios in digital form against predetermined threshold signals also in digital form and individual to the pixels of a single scan sweep. Such an arrangement accommodated the changes in pixel magnitude such as in a bottle wall at the shoulder where the general change is uniform around the circumference of the bottle and thus at a uniform height region on the multiple vertical sweep of the bottle.

Large objects which are transparent, such as the viewing faces of cathode ray tube faceplates, can be inspected employing line scan techniques. In U.S. Pat. No. 4,606,634 there is disclosed an arrangement for translating the viewing face of a faceplate through an optical system including a source of illumination on one side and means to pass light through the viewing area to a plurality of line scan cameras having their aligned photodiode arrays aligned. In the case of faceplate viewing surfaces, optical quality requirements dictate high resolution inspection. For example, three cameras each with one thousand twenty four aligned photodiodes are disclosed in U.S. Pat. No. 4,606,634, to span the minor dimension of a rectangular faceplate.

The interpretation of large amounts of data as from long linear arrays of diodes and large numbers of sweeps of such arrays is accomplished according to this invention by high pass filtering of the analog video signal or the log of the analog video signal such that the effect of slowly changing light intensity is eliminated and only abrupt changes in intensity produce signals which are passed to the circuitry for detecting the magnitude of change or a threshold ratio of change. The ratio of the change in signal magnitude at a defect to adjacent signal magnitudes is ascertained by scanning a linear array of photosensitive diodes whose peak value signals produce an analog video signal envelope representing light intensity from discrete areas on the object under inspection which are individual to the diodes and fall in a band on the object corresponding to the linear array. That analog signal is amplified in a logarithmic amplifier whose output is high pass filtered to pass only logarithmic signals representing abrupt changes in light intensity. The passed logarithmic signals are converted to digital form and applied to a comparator in which they are compared to a threshold signal representing the digitized logarithm of the threshold ratio. As will be explained, this high pass filtered log signal represents a ratio of the signal difference between the currently scanned photosensor and the video signal envelope developed from the scan of preceding photosensors which can be considered a weighted average of the logarithms of those photosensor signals. The comparator will respond to deviations from the threshold by issuing a detection signal for the event signal and enabling storage of data pertinent to that event signal.

True signal magnitudes can also be segregated for abrupt light intensity changes or events so that only those magnitudes are processed by applying the analog video signal to a high pass filter which passes only the event signals at their magnitude of deviation from the video signal envelope developed from the scan of preceding photosensors. Again this video signal envelope for photosensors which are receiving constant or gradually changing illumination can be considered to be a weighted average of those signals. That magnitude can be stored and processed to produce significant inspection data. One such form of data is the length of strings of events in a sweep and the size of blobs made up of contiguous events in adjacent sweeps to indicate the size of defects. Sizing is accomplished by processing adjacent event signals so that only those signals of a magnitude exceeding one half the peak magnitude deviation from non-defect light intensities, are treated as representing the defect area.

In the system with which these data recognition, comparison and magnitude signals are produced, a line scan camera is employed as the source of analog video signals. The camera scan of its diode array is clocked and a counter generates diode addresses. At the end of each scan the diode counter is reset and the sweep number is advanced to provide a sweep address to a counter which was reset at the beginning of an inspection sequence.

The signals from diodes subject to scan interrogation which are of a threshold level are classified as "events" and actuate an event counter and event address. The addresses drive memories to store events as to location and magnitude. These data are saved for processing in a central processor which is programmed to accept, reject, or grade the article under inspection and collects data as to the nature of defects represented by the detected events, the location, the size of such defects, their density as to region of the viewing area and the like.

The above and additional features of this invention will be appreciated more fully from the following detailed description when read with reference to the accompanying drawing in which.

Figure 1:
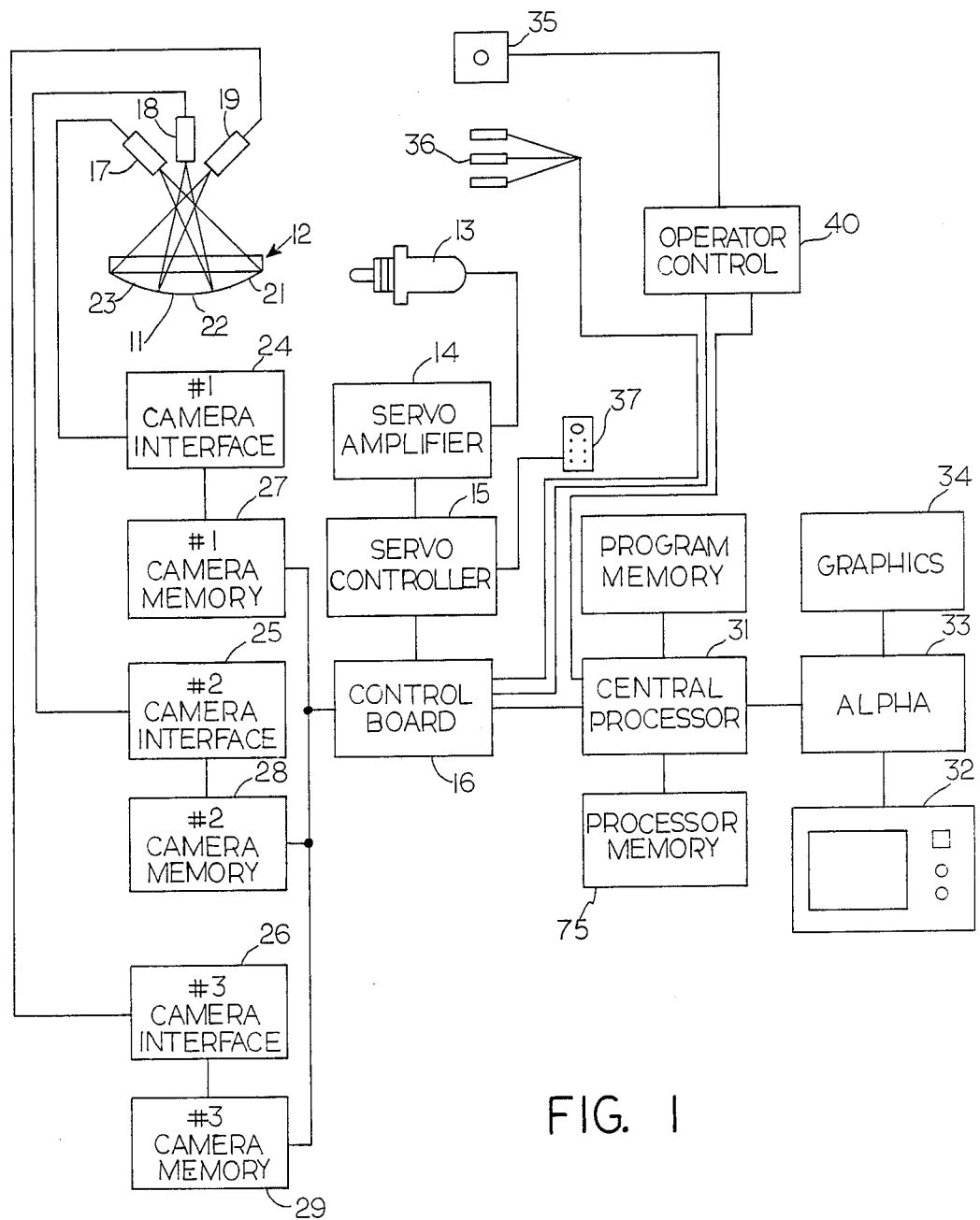
FIG. 1 is a block diagram of a system according to this invention fo inspecting CRT faceplates.

A typical system employing the method and apparatus of this invention is shown in FIG. 1 in conjunction with an electrooptical faceplate inspection system for detecting stones and blisters in the viewing region 11 of a flanged faceplate 12. Faceplate 12 is mounted on a cradle and in an optical system as illustrated in U.S. Pat. No. 4,606,634, the disclosures of which are incorporated herein by reference (not shown), which rocks it into and out of the paper, as viewed in FIG. 1, under the control of a servo motor 13 driven by a servo amplifier 14 from a servo controller 15. Servo controller is coordinated with inspection camera operations from a control board 16 so that scans of transverse bands of the viewing region 11 are made as the bands are positioned in the optical path to the cameras by the servo drive of the cradle. Typically a twenty-five inch rectangular faceplate (diagonal dimension) has a fifteen inch width and a twenty inch length and the system of cameras 17, 18 and 19 is arranged with three linear arrays of diodes each comprising two thousand forty-eight diodes which when aligned with a slight overlap provides six thousand pixels or viewed discrete areas along the aligned array of fifteen inches of the minor dimension of the viewing region 11. The major dimension of viewing region 11 is scanned in eight thousand scans as the faceplate is traversed through the band field of view of the cameras.

The number 1, 2 and 3 cameras 17, 18 and 19 are shown focused at regions 21, 22 and 23 respectively on the inner surface of faceplate viewing region 11 and a source of uniform light intensity (not shown) is directed on the outer surface of region 11 from below as viewed in FIG. 1. Each camera has an aligned array of photodiodes (not shown) which issue electrical signals as a function of the light intensity they receive from their respective discrete areas in region 21, 22 or 23 as the case may be and thus as a function of the degree of transparency of those points or areas corresponding to the pixels in an optical system that selectively excludes refracted light as described in U.S. Pat. No. 4,606,634.

The analog signal representing light emanating from each discrete area is scanned in the respective camera as the diode array is scanned under control of a camera clock which can be on control board 16. That analog video signal is of a stepped form produced by internal sample and has a circuitry and is processed for the system in individual camera interface circuits 24, 25 and 26 which ascertain those signals representing reduced pixel illumination as to threshold levels, diode and scan number and thus pixel position. Only those signals which may be indicative of a defect are recognized and designated "events" for the remainder of the processing functions of the system.

The magnitude, diode number and scan number of events are stored in respective camera memories 27, 28 and 29 and are accessed through control board 16 by the central processor 31 to develop inspection information. At the end of an inspection sequence, an interrupt is provided to enable the camera memories to be read out to the processor memory 75. The central processor can issue grade classifications for the faceplates based upon the number of events, the location of the events and the magnitude of the events and any combination of these factors. The exemplary system has a resolution capacity of about 3 mils and thus will detect defects which are essentially invisible to the human eye. Further, it will detect longer defects represented as a string of events which may or may not be significant to the utility of a display tube produced from the faceplate.

Inspection system outputs can include a display of the viewing region 12 with the defects portrayed as to location, size and shape on a monitor 32, as data in alpha numeric form and graphically as developed by control circuits 33 and 34 coupled between the central processor 31 and monitor 32.

Additional adjuncts of the system can include control switches, represented by start button 35, cradle limit switches 36, servo manual control 37, reset buttons, keyboards to set parameters, call up program menus and the like, many of which are not shown and are represented by operator control 40.

Figure 2:
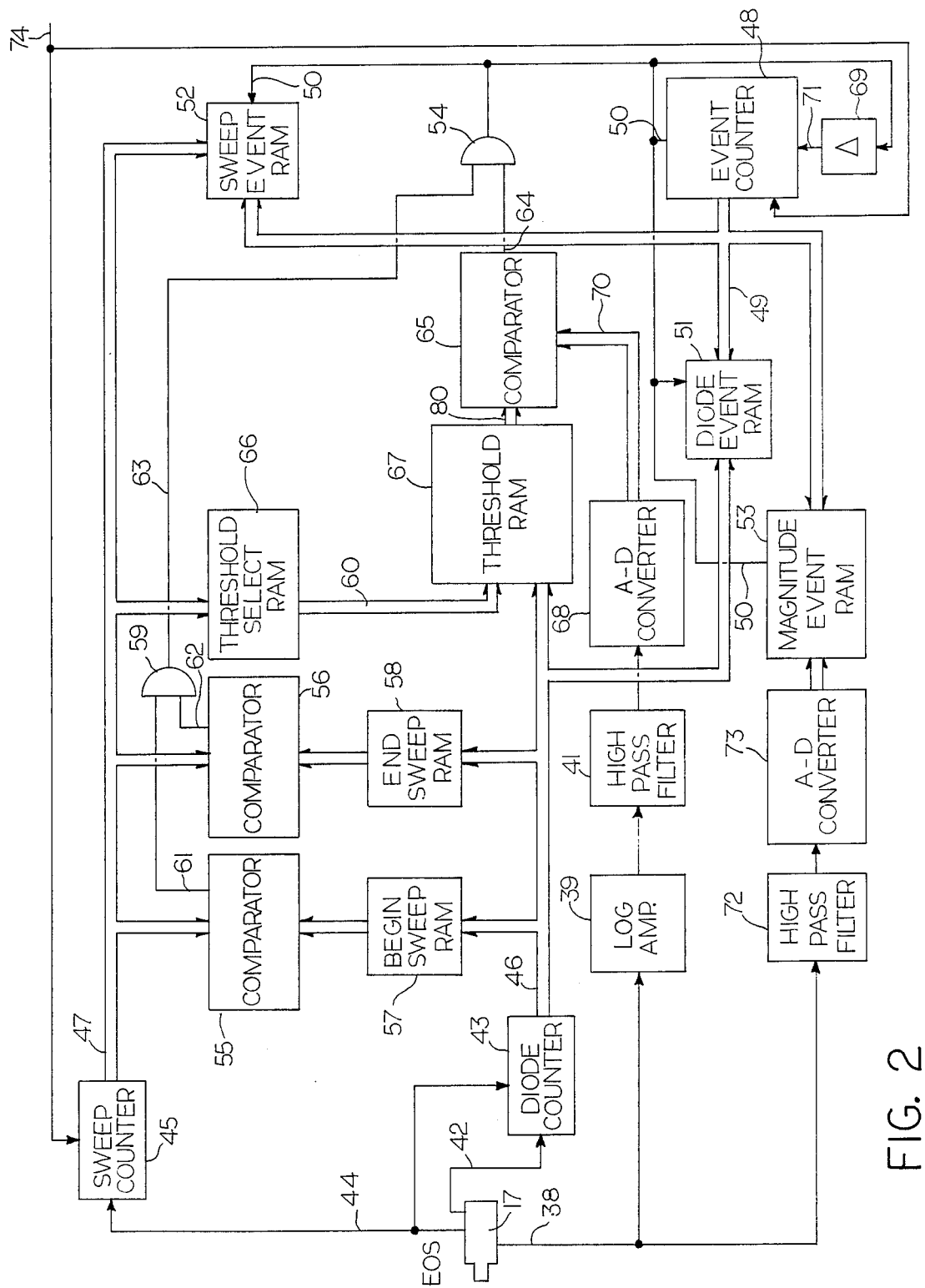
FIG. 2 is a block diagram of the camera interface and memory circuitry of FIG. 1 in which logic functions according to this invention are performed.

A block diagram of a camera interface and a camera memory block of FIG. 1 is shown in FIG. 2 wherein inputs from the camera 17 and its controls include the analog signal input 38 which supplies signals from the currently scanned camera diode to logarithmic amplifier 39 and high pass filter 72, camera clock input 42 to diode counter 43, and end of sweep input 44 to sweep counter 45 and the reset of diode counter 43. Camera clock input 42 applies pulses corresponding to the scan steps for scanning the linear array of diodes in the camera and this results in an advancing pulse to the diode counter 43 which places that counter at the diode number of the currently scanned diode and thus the pixel number or discrete area number on faceplate 11 surface region 21 subject to inspection. The diode counter 43 is reset at the end of each sweep of the diode array by a signal from the end of sweep input 44 so that its count starts from its reset value for each scan and it issues on "Diode Number" bus 46 the digital number designating the diode currently scanned. That end of sweep signal is derived from the camera scan control at the end of each diode array sweep to add a count to sweep counter 45 identifying the next scan number on "Sweep Number" bus 47. A reset of sweep counter 45 is issued at the end of each inspection routine by the central processor 31.

The significant data to be created in the system is the occurrence of events or sensed optical changes indicative of defects or blemishes. Event RAM address data is derived from event counter 48 over "Event RAM Address" bus 49 to cause the event memories to store the diode number of the event in "Diode Event" RAM 51, the sweep number of the event in "Sweep Event" RAM 52 and the magnitude of the event in "Magnitude Event" RAM 53. These event circuits are enabled through "Event Enable" AND 54 in response to a logarithmic signal from the currently scanned diode passed by high pass filter 41 which is of a magnitude at least equal the predetermined threshold signal magnitude for that diode during that scan, provided the signal is derived from a diode within the predetermined window for that sweep.

The window of acceptance of diode signals as events is defined by sweep and diode numbers for the beginning and end of each sweep by "Begin Window" comparator 55 and "End Window" comparator 56. The effective sweep number is supplied in digital form on bus 47 to each of comparators 55 and 56. The currently scanned diode number on bus 46 is supplied to "Begin Sweep" RAM 57 and "End Sweep" RAM 58. A predetermined, individual sweep number to begin the sweep window for each diode is set in RAM 57 and a predetermined, individual sweep number to end the sweep window for each diode is set in RAM 58. Each of RAMs 57 and 58 are arranged to issue digital sweep numbers to their respective comparators 55 and 56 for each digital diode number from "Diode Count" bus 46. When the sweep number on bus 47 from "Sweep Counter" 45 is equal to or exceeds the sweep number in the RAM 57 at the diode count address, comparator 55 issues a "true" enable signal on lead 61 to "Window Defining" AND 59 which, if enabled by a "true" state on lead 62, is gated through lead 63 to enable "Event Enable" AND 54. Comparator 56 issues a "true" signal on 62 until the diode address of the sweep applied to "End Sweep" RAM 58 issues the sweep number signal to "End Window" comparator 56 causing it to remove the true state on lead 62. When lead 62 goes "false" as a result of a sweep count from RAM 58 at or above the sweep count on bus 47, AND 54 is inhibited to inhibit AND 54.

Coincidence of enabling signals on leads 63 and 64 gates AND 54 to trigger event counter 48 and issue "Save Event Data" signals on lead 50 to each of the sweep event RAM 52, diode event RAM 51 and magnitude event RAM 53. A logarithmic video signal which is passed by the high pass analog filter and meets the predetermined threshold magnitude results in a signal out of comparator 65.

Each sweep can have threshold levels set for its individual diodes according to the sweep number on bus 47 to threshold select RAM 66. RAM 66 provides look up tables from which thresholds are set. A convenient arrangement is to provide four available series of threshold levels in "Threshold" RAM 67, one of which is selected via the output 60 of "Threshold Select" RAM 66 for each sweep number. The diode number currently subject to scan is applied to threshold RAM 67 from "Diode Number" bus 46 so that the threshold digital signal level is issued for the effective sweep and diode to comparator 65. Analog to digital converter 68 responds to high pass filtered logarithm of the analog magnitude signal from the diode currently subject to scan as issued by logarithmic amplifier 39 through high pass filter 41 to provide a digital magnitude signal for each passed signal to comparator 65 on "Logarithmic Magnitude" bus 70. If that magnitude is at least the threshold digital signal set by threshold RAM 67, comparator 65 will pass an enable signal on lead 64 to event enable AND 54.

AND 54 sets the memory location of the sweep number, diode number and magnitude of the event through the event counter 48 on bus 49 as an event ram address for the "Sweep Event" RAM 52, "Diode Event" RAM 51 and "Magnitude Event" RAM 53. It issues a "Save Signal" on lead 50 to each of RAMs 52, 51 and 53 so that the current sweep number on bus 47 is stored at its designated memory location in RAM 52, the current diode number from which the event signal was derived as present on bus 46 is stored at its designated memory location in RAM 51 and the event magnitude is stored in RAM 53 at its designated memory location. "Save Signal" from AND 54 increments the event counter 48 after a delay sufficient to enable storage of the data in RAMs 52, 51 and 53 by passing that signal through delay 69 to the increment input 71 of counter 48.

The absolute magnitude of the event as received from the currently scanned diode of the camera at camera analog input 38 is passed by high pass filter 72 to analog to digital converter 73 from which it is passed in digital form for storage in "Magnitude Event" RAM 53.

Thus those events within the window defined between the limits set by "Begin Sweep" RAM 57 and "End Sweep" RAM 58 diode and sweep numbers which meet the threshold of magnitude defined for the diode and sweep number by "Threshold" RAM 67 are saved in "Sweep Event" RAM 52, "Diode Event" RAM 51 and "Magnitude Event" RAM 53 for processing by central processor 31.

Central processor 31 processes the data saved in processor memory 75 after it has been transferred to that memory from "Sweep Event" RAM 52, "Diode Event" RAM 51, and "Magnitude Event" RAM 53. Control board 16 generates the signals to the cameras to acquire data, communicates with the servo controller to issue instructions such as "Center Cradle", "Cycle Cradle" or "Return to Home Position" and to pass saved data to the central processor and its processor memory. The executing program for the central processor board 31 issues commands to acquire data from the memories, analyzes the data and issues a decision about the inspected faceplate based on that analysis. It also communicates with the operating attendant through the video subsystem. At the end of an inspection routine analysis, the central processor issues a clear signal on lead 74 to the sweep counter 45 and the event counter 48 to reset those counters for the next inspection cycle.

The video signals from each of cameras 17, 18 and 19 are developed from a relatively uniformly illuminated image area as disclosed in U.S. Pat. No. 4,606,634. Image area illumination may have slowly changing light intensity across the image or on some regions of the image area as where the thickness of the cathode ray tube faceplate varies from the center toward the outer edge in the illustrative optical inspection process or where a glass bottle wall thickness variation or contour changes, as in the heel and shoulder region of the bottle. Further, there may be nonuniformity resulting in slow changes in source illumination across the image area.

Illumination invariant processes previously proposed have involved cumbersome and slow techniques of signal manipulation involving digital conversion storage and comparison of successive video signals in line scan processing which impose unwarranted limitations on the process disclosed here. According to this invention the analog video signal is high pass filtered to reduce the effects of optically induced slowly changing light levels thereby enabling the image features of interest, such as opaque defect edges in the glass of a faceplate, to be the dominant signal features at high spatial frequencies. Image features in dimmer areas are given the same weight as they would have in bright areas by combining high pass filtering with log amplification. Since the system identifies the location of detected features of interest, the event signals, by filtering with log amplification, its processing of collected data can be arranged to compensate for predetermined light intensity levels anticipated for those locations in developing the inspection evaluation of the product. Direct signal magnitude sensing enables values to be stored which can be compensated in processing, further such magnitude values are available for defect sizing.

Figure 3:
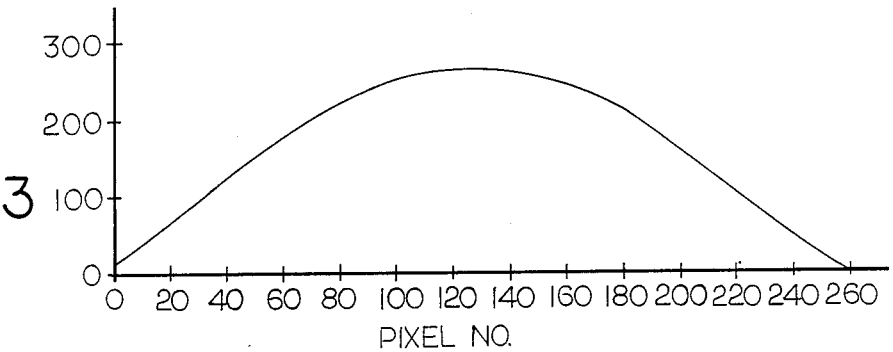
FIG. 3 is a plot of a video signal derived from a scan across a field in which light is slowly changing in intensity.
Figure 4:
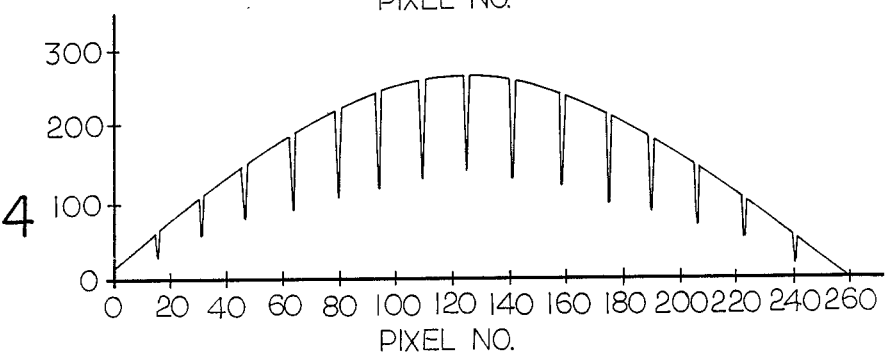
FIG. 4 is a plot of a video signal for the field of FIG. 3 with dark objects located along the field each of which reduces the light intensity at its peak to one half the adjacent intensity.

In order to explain the advantages of analog video signal processing according to this invention, FIGS. 3 and 4 should be considered. In these plots the pixel signals of a linear array of photodiodes are represented to develop a video signal envelope according to the light flux on the individual element as they are scanned, assuming for illustrative purposes that the sensors linearly convert the illumination they receive into voltages. Thus FIG. 3 shows the signal resulting from the scan of slowly varying illumination induced by nonuniform lighting and optical effects in an empty field. FIG. 4 shows the effects of small dark objects in the same field as FIG. 3 where those objects transmit or reflect, depending upon the nature of the sensed illumination, at a value of one half so that the field magnitude is unity everywhere except in the presence of those objects and is one half at the object locations. In this varying field, as illustrated, there is no linear threshold which can differentiate between background and all of the dark objects simultaneously since a threshold set to sense the object at about the one hundred and twentieth pixel, the maximum background, would sense the background prior to the fortieth pixel and subsequent to the two hundred and twentieth pixel, the half maximum background limits.

Figure 5:
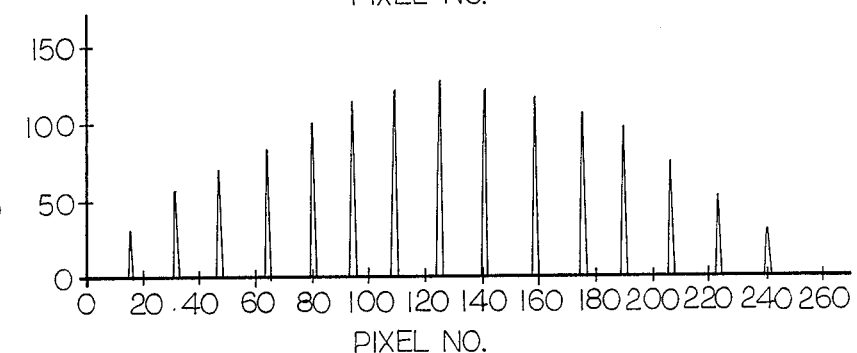
FIG. 5 is a plot resulting from the filtering of the signal of FIG. 4 with a high pass filter.

A high pass filtering of the signal plotted in FIG. 4 produces an idealized signal as shown in FIG. 5. Again no losses are assumed for illustrative purposes and polarities have been chosen to accommodate the signal as passed from high pass filter 72 to the analog to digital converter 73 of FIG. 2. The high pass analog signal filter 72 is chosen to have a time constant which is long relative to individual pixel scan intervals. Pixel scan rate in an exemplary system is five megapixels per second and is fixed in frequency. An envelope video signal is established by the scan of a succession of pixels effectively to establish a weighted average signal representative of the light intensity over that group of pixels. The high pass filter 72 passes only abrupt changes in signal magnitude from the thus established weighted average and may respond to a group of such signals applied in sequence representing a string of pixels or discrete areas on the object in the optical system from which light emanates at a lower intensity than the weighted average. The signal magnitudes passed are absolute differences from the average and will vary if source illumination level varies or the average illumination emanating from the discrete areas varies. Thus signals are issued to magnitude event RAM 53 when simultaneously enabled and assigned an address by the presence of an event signal to issue a "Save Data" signal on lead 50 and an event address on bus 49.

Figure 6:
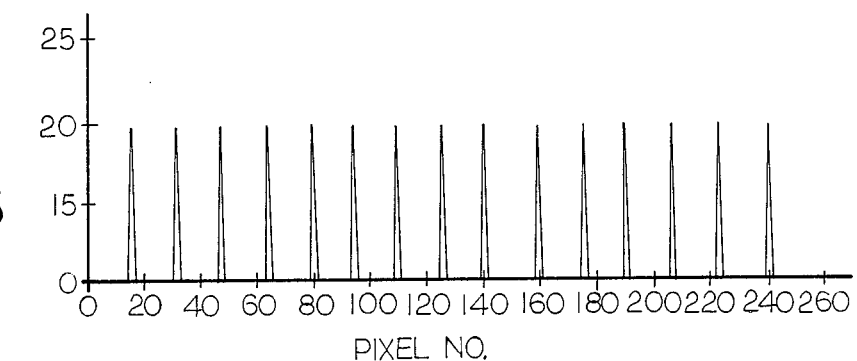
FIG. 6 is a plot resulting from the log amplification of the signal of FIG. 4 and the filtering of the logarithmic signal with a high pass filter.

Illumination invariant signals are illustrated in the plot of FIG. 6 wherein the fifty percent transmission or reflection, as the case may be, results in pulses of uniform magnitude for all of the levels of illumination shown in FIG. 4 by virture of the high pass filtering of a logarithmic amplification of the signal of FIG. 4. Log amplifier 39, for example, produces a signal for all dark objects having illumination values half of the background illumination and therefore differs from its proximate logarithmic background by the same logarithmic value. When high pass filtered so that only the darkened area signals of the logarithmic signals are passed, uniform signal magnitudes are produced for all defects of similar light transmission or reflectance and a threshold signal level can be established without dependence upon the illumination levels. Again the background illumination intensity is established by the scan of a succession of pixels effectively to establish a weighted average light intensity signal and thus the logarithm of such a signal. The analog to digital converter 68 converts the signal for application on event bus 70 to comparator 65 which also receives a digital threshold signal from RAM 67 so that when the threshold signal is equaled or exceeded comparator 65 issues an event signal on lead 64 to set event counter and the event memories.

The magnitude of the event and the logarithmic value triggering the event are polarity corrected for the a-d converters 68 and 73 by rectifier bridges (not shown). Such corrections can provide full wave rectification so that deviations from the background illumination level signal of either an abrupt increase or decrease in illumination will register as an event or by appropriate wiring a half wave rectification of either polarity can provide the desired polarity at the converter. In the example discussed above, the rectifier bridge is responsive to dark objects in a bright field to produce the event triggering signal and event magnitude signal.

In the case of strings of events which are long, the signal envelope tends toward the event magnitude. However, the time constant of the high pass filter is chosen to be long enough that the event signals continue to be generated over the entire length of any string emanating from the object. Such long strings are compressed in the data gathering process by means shown in U.S. patent application Ser. No. 058,208 filed herewith in the name of Thomas F. Michalski and David J. Bauer entitled "Method of and Apparatus for Video Data Compression" wherein events are counted and upon achieving a predetermined count within the event detection and magnitude determination capacity of the high pass filter processing only identification of diodes defining the length of the string of events are saved, no magnitude data is saved and a marker for data compression is effective to enable processing of the saved data by central processor 31.

The events identified as to diode number, sweep number and magnitude are processed to identify defects such that events which are in proximity to each other in a sweep are identified as a string. Strings in different sweeps in proximity are identified as blobs. Events making up a blob are counted to ascertain if the respresented defect is of a size to warrant rejection of the faceplate or grading of the faceplate to a secondary quality. In precise inspections the diode limits which truly represent the limits of the defect are identified employing the magnitude values stored in magnitude event RAM 53 by eliminating optical fringe effects through the process of ascertaining the maximum magnitude of an event within a blob, establishing a half maximum threshold magnitude, and identifying those events which exceed that half maximum threshold as the boundaries of the blob.

Figure 7:
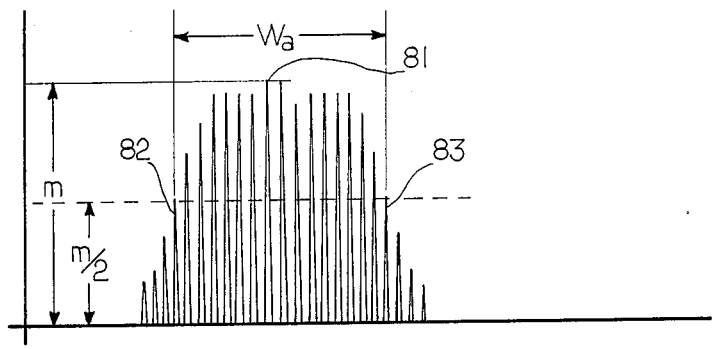
FIGS. 7, 8 and 9 are plots of a filtered video signal for scans of a portion of a faceplate containing a dark object to illustrate the use of the signal to determine the true width of the dark object.
Figure 8:
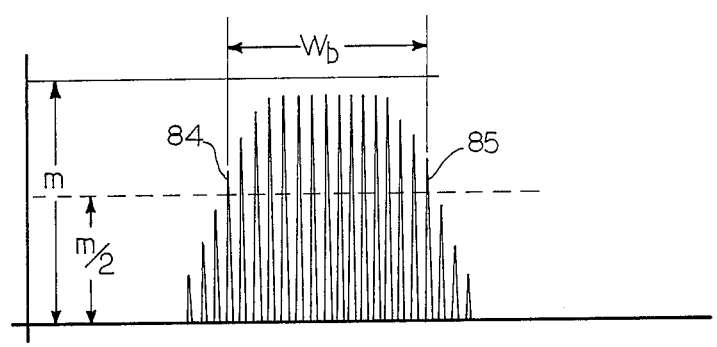
Figure 9:
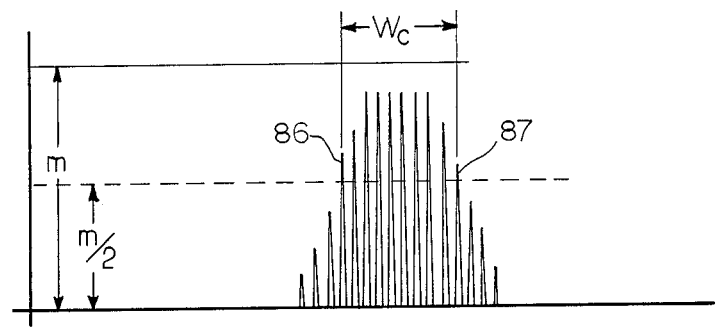
Figure 10:
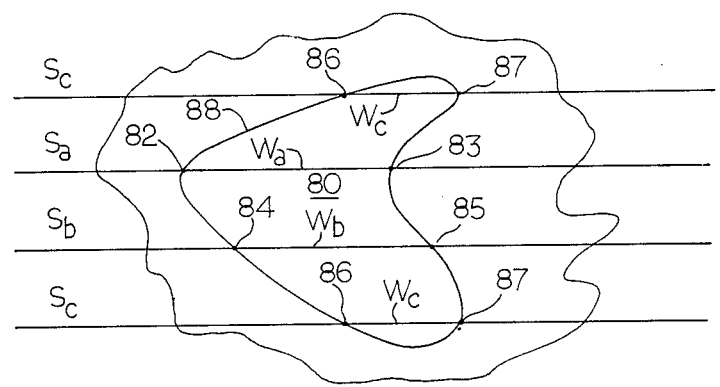
FIG. 10 is a broken out plan view of the portion of the faceplate scanned to obtain the plots of FIGS. 7, 8 and 9.

FIGS. 7 through 10 illustrate the process of establishing blob boundaries based upon the collected data. FIGS. 7, 8 and 9 represent the signal after analog processing for three sweep patterns for strings of events spaced across a blob 80 in a portion of a faceplate as represented in FIG. 10 such that the sweep of FIG. 9 illustrates sweep $S_c$ at the top and bottom of the blob 80, the sweep of FIG. 7 represents sweep $S_a$ and the sweep at FIG. 8 represents sweep $S_b$. It will be noted from FIGS. 7, 8 and 9 that the high resolution offered by the closely spaced diodes in the linear array result in a sensing of optical fringe effects and thus a gradual change in light intensity near the blob boundaries. Thus the full change in light intensity is not effective until pixels well within the blob boundaries are interrogated. It can be shown that the true boundary is located at essentially the 50% magnitude point hence the m/2 threshold is the point at and above which pixels or diode signals are considered to be within the blob boundary 88. In the illustration the maximum event magnitude appears in sweep $S_a$ at 81 and sets magnitude value m for the blob from which the half maximum magnitude threshold m/2 is set to establish which pixel signals define the blob boundaries. In sweep $S^a$ and FIG. 7 pixel 82 defines a left boundary point and pixel 83 the right boundary point and those pixels and pixels between those pixels are counted to constitute string length $W_a$. In sweep $S_b$ and FIG. 7 pixels 84 and 85 define left and right boundary points and the limits for string $W_b$. $S_c$ pixels 86 and 87 are boundary points and limits for strings $W_c$. Other event strings may appear intermediate the sweeps represented to define the blob 80, more precisely and establish its boundary 88 as shown on FIG. 10.

Figure 11:
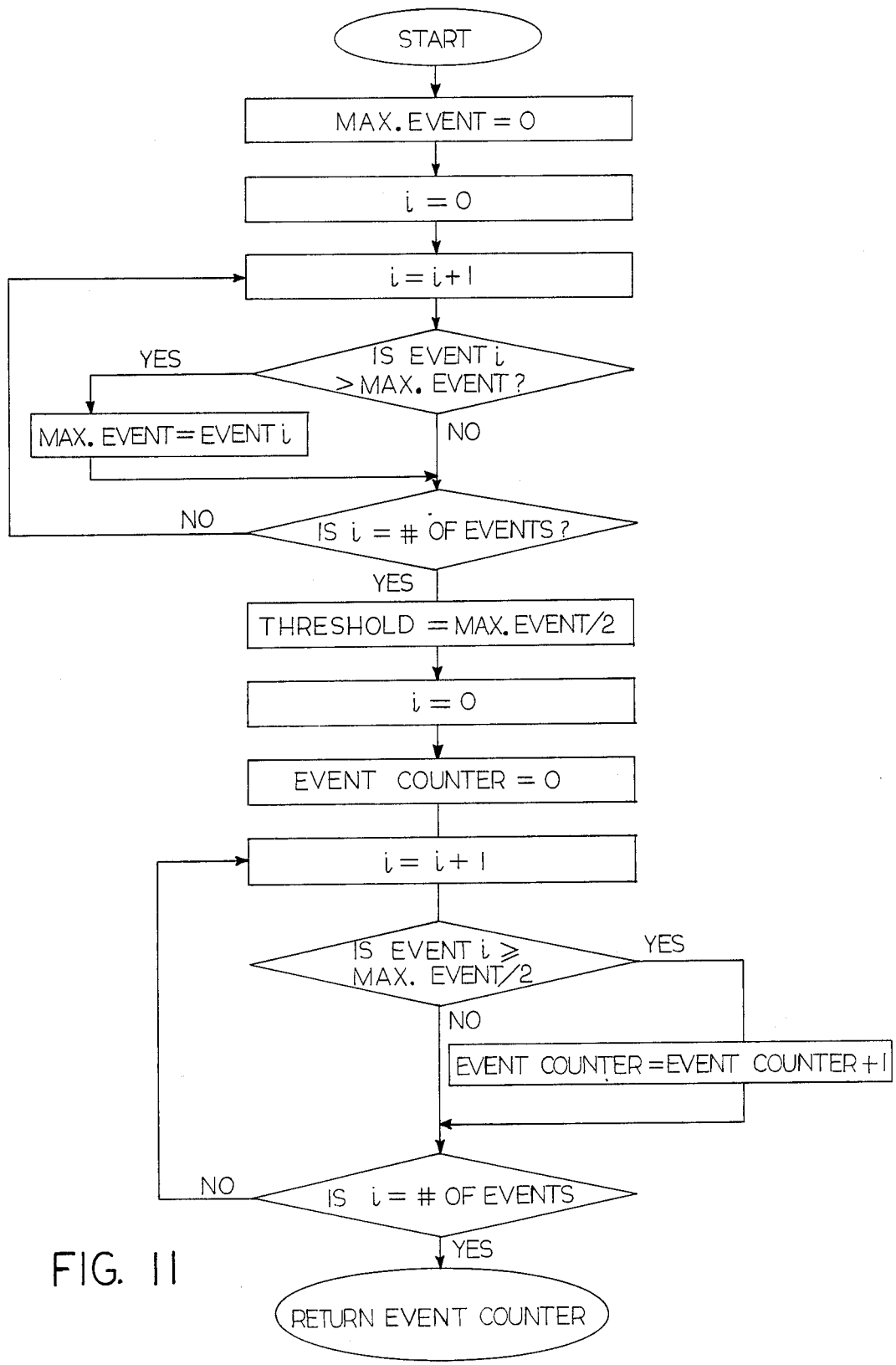
FIG. 11 is a flow diagram of the signal processing to ascertain dark object area.

FIG. 11 illustrates a processing flow chart for ascertaining defect size by count of the number of events in contiguous strings of proximate sweeps. The magnitudes, diode numbers, and sweep numbers are derived from RAMs 53, 51 and 52 respectively are transferred to processor memory 75 and are processed in central processor 31 to find the number of events greater than one half the maximum magnitude of all events for the blob. Strings of events assigned to a blob are assembled by the proximity of diode counts for proximate strings according to the central processor program which may assign strings with overlaying events which are spaced several scans apart. Thus as shown in the drawings, the event signals occur on the same diodes for proximate sweeps and are marked in memory by blob assignment.

The processing of strings and thus events assigned, a blob involves setting a magnitude to zero (maximum event=0), setting a counter to zero (i=0), incrementing the counter, and interrogating the event magnitude for i (is $event_i$ magnitude greater than maximum event magnitude). If the answer is yes, the maximum event magnitude is set to the magnitude of $event_i$ and the process returns to the event count comparison to ascertain if all events associated with the blob have been considered. If the $event_i$ magnitude is not greater than the maximum event magnitude, the decision proceeds directly to the event count comparison. If the event count is not equal to the total count of the events in strings assigned to the blob, the process recirculates by incrementing the event interrogation.

After all events assigned to a blob have been interrogated and the maximum event magnitude ascertained, threshold magnitude blob measurement is set at one half maximum event magnitude and the event count for the blob is again set to zero. The blob measurement event count is set to zero. The event count is incremented one event and the interrogation made "is event$_i$ magnitude equal or greater than threshold magnitude". If yes, the blob measurement event$_i$ count is advanced one and the decision point "is event count equal to total events" in blob entered. If the event$_i$ magnitude is less than threshold magnitude, then the program proceeds directly to the decision point "is event$_i$ count equal to total events". If the event$_i$ count is not equal to the total events assigned to the blob, the program returns to increment to the next event and the magnitude of that event compared to the threshold. Once all events assigned to the blob have been interrogated and those events of a magnitude equal to or exceeding the threshold magnitude counted, that count is utilized to evaluate the faceplate or at least the defect represented by the blob and the process event count and evaluation initiated for the next blob in the faceplate. Thus the entire faceplate is evaluated for blob size in a succession of such sequences utilizing absolute magnitudes of events as derived from RAM 53.

The system has been illustrated as applied to a cathode ray tube faceplate inspection, however, it should be appreciated that it can be utilized in other applications where the detection of optical deviations in an object is to be undertaken either as light transmitting or light reflecting deviations or objects are involved. Line scan cameras having linear arrays of optical sensors can be arranged to generate analog signals representing the magnitude of light received from discrete areas of the object corresponding to individual sensors. The linear array thus senses a band of discrete areas of light emanating from the object and is sampled by scanning the array at a fixed frequency to produce an analog video signal made up of individual pixel impulses. The analog video signal is subject to a high pass analog filter which blocks signals from sensors which represent areas which are of the same general magnitude as signals derived from nearby areas. These signals represent a weighted average of the light intensity on prior scanned sensors, the background lighting level, as a video signal envelope. The filter passes signals which are of a substantially different magnitude from the weighted average signal level, the pixel signals from discrete areas having an illumination level substantially different from the background. A series of such pixel signals are passed since the filter has a time constant which is long relative to the period of the frequency of scanning the sensors of the linear array. Such passed signals have magnitudes which are a function of the difference in illumination emanating from the discrete areas they represent from the adjacent areas from which the background level of illumination is established and the weighted average signal level derived.

The high pass analog signal filtering is effective to isolate deviations in absolute signal magnitude and is utilized to obtain data of the mangnitude of illumination deviation. Such filtering is also employed to develop background illumination invariant detection of abrupt changes in illumination by generating a logarithmic signal of the analog video signal and filtering that logarithmic signal for detecing a threshold level of change of signal level from the background or weighted average signal. Those signals achieving the threshold, termed events, actuate data collection for magnitudes and location of the optical deviations.

Line scan inspection combined with relative motion between the optical system and the object within the system facilitates inspection of non-planar objects by a plurality of sweeps which are counted as a means of locating the discrete area on the object from which events are developed. Thus a bottle or tube might be inspected employing these techniques by rotating the bottle in the optical system so that successive bands of discrete areas along the longitudinal axis can be swept.

It is to be appreciated that the above disclosure is exemplary and is not to be read in a limiting sense since high pass filtering of absolute and logarithmic analog video signals can be utilized in defect detection in other systems without departing from the spirit and scope of this invention.

What is claimed is:

1. An apparatus for detecting optical deviations in an object comprising a linear array of optical sensors each providing an analog signal representing the magnitude of light received from a corresponding discrete area along a band of discrete areas on the object; means to sample said sensor signals serially at a fixed frequency; a high pass analog filter for said signals which blocks signals derived from said sensors representing areas which are of the same general magnitude as signals derived from sensors representing nearby areas, said filter passing signals derived from said sensors representing areas which are of a substantially different magnitude than signals derived from sensors representing nearby areas, said filter having a time constant which is long relative to the period of said fixed frequency.

2. An apparatus according to claim 1 including an analog to digital converter for converting signals passed by said filter to digital form.

3. An apparatus according to claim 1 including means to generate a threshold signal representative of a signal magnitude for a predetermined optical deviation; and means to compare the signal passed by said filter with said threshold signal to issue a signal indicative of the predetermined optical deviation in response to the signal passed by said filter having a magnitude of at least said threshold signal.

4. An apparatus according to claim 1 including a logarithmic amplifier for the analog signals from said sensors to supply the signals to the high pass analog filter.

5. An apparatus according to claim 3 including a logarithmic amplifier for the analog signals from said sensors to supply the signals to the high pass analog filter.

6. An apparatus according to claim 5 including an analog to digital converter for converting signals passed by said filter to digital form for processing by said means to compare.

7. An apparatus according to claim 6 including a second high pass analog filter for said signals from said sensors which blocks signals from said sensors representing areas which are of the same general magnitude as signals from sensors representing nearby areas, said second filter passing signals derived from said sensors representing areas which are of a substantially different magnitude than signals derived from sensors representing nearby areas, said second filter having a time constant which is long relative to the period of said fixed frequency; a second analog-to-digital converter for signals passed by said second filter; a signal storage means for storing signals from said second analog-to-digital converter; and means to enable said signal storage means in response to a signal from said means to compare.

8. Apparatus according to any of claims 1 through 7 wherein said object is of glass and said deviations are representative of defects in said glass and including means to illuminate the band of discrete areas on the object with a relatively uniform light flux; means to move said linear array of sensors and said object relative to each other to expose said linear array to a succession of bands of discrete areas on the object; and means to actuate said means to sample repetitively to develop a plurality of sweeps of different bands on the object.

9. The method of inspection for defects in successive objects comprising backlighting the object with light of generally uniform intensity; optically scanning a band of discrete areas extending across a region of the object to be inspected; moving the object and scanning means relative to each other to subject a plurality of bands on the object to the optical scanning; generating an analog pixel signal for each discrete area of the object scanned having a magnitude which is a function of the light emanating from the discrete area; high pass filtering the analog signals to pass only those pixel signals which abruptly deviate in magnitude from a weighted average pixel signal magnitude of previously scanned discrete areas; digitizing the magnitude of the passed pixel signals; generating an analog logarithmic pixel signal for each discrete area of the object scanned; high-pass filtering the analog logarithmic signals to pass only those pixel signals which abruptly deviate in magnitude from a weighted average logarithmic pixel signal magnitude of previously scanned discrete areas; digitizing the passed logarithmic signals; issuing a digitized threshold signal value predetermined and individual for the discrete area being scanned; comparing the passed logarithmic signal with the individual threshold signal to develop an event signal when the passed logarithmic signal is of the threshold magnitude; and storing the magnitude of the passed pixel signals in response to an event signal.

10. The method according to claim 9 including the steps of identifying each event by location; assembling proximate events into a blob; ascertaining the maximum event magnitude within a blob; and counting the number of events within a blob of a magnitude of at least one half the ascertained maximum event magnitude as a measure of blob size.

11. The method according to claim 9 wherein each event location is identified by scan sweep count and scan pixel count, and wherein proximate events are assembled as strings of events in scan sweeps and as proximate strings in adjacent scan sweeps.

* * * * *